United States Patent
Yoo et al.

(10) Patent No.: US 12,146,879 B2
(45) Date of Patent: Nov. 19, 2024

(54) CAPACITIVE BIOSENSOR FOR IDENTIFYING A MICROORGANISM OR DETERMINING ANTIBIOTIC SUSCEPTIBILITY

(71) Applicants: INDUSTRY-ACADEMIC COOPERATION FOUNDATION, YONSEI UNIVERSITY, Seoul (KR); PROTEOMETECH INC., Seoul (KR)

(72) Inventors: Kyung Hwa Yoo, Seoul (KR); Nal Ae Han, Busan (KR); Bong Jun Kim, Gyeonggi-do (KR); Sun Mi Lee, Seoul (KR); Kook Jin Lim, Seoul (KR); Jeseung Oh, Gyeonggi-do (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 1074 days.

(21) Appl. No.: 17/068,148

(22) Filed: Oct. 12, 2020

(65) Prior Publication Data

US 2021/0140963 A1  May 13, 2021

Related U.S. Application Data

(62) Division of application No. 15/675,953, filed on Aug. 14, 2017, now abandoned.

(30) Foreign Application Priority Data

Aug. 12, 2016 (KR) .................. 10-2016-0103015

(51) Int. Cl.
| | |
|---|---|
| *G01N 33/569* | (2006.01) |
| *C12Q 1/04* | (2006.01) |
| *C12Q 1/18* | (2006.01) |
| *G01N 27/22* | (2006.01) |
| *G01N 33/15* | (2006.01) |
| *G01N 33/543* | (2006.01) |
| *C12Q 1/00* | (2006.01) |
| *G01N 33/00* | (2006.01) |

(52) U.S. Cl.
CPC ............ *G01N 33/569* (2013.01); *C12Q 1/04* (2013.01); *C12Q 1/18* (2013.01); *G01N 27/227* (2013.01); *G01N 33/15* (2013.01); *G01N 33/54366* (2013.01); *G01N 33/5438* (2013.01); *G01N 33/56911* (2013.01); *C12Q 1/00* (2013.01); *G01N 27/226* (2013.01); *G01N 33/00* (2013.01); *G01N 2500/10* (2013.01)

(58) Field of Classification Search
CPC ..................................................... G01N 33/569
See application file for complete search history.

(56) References Cited

PUBLICATIONS

Abeyrathne et al (Analyst vol. 141, pp. 1922-1929) (Year: 2016).*
Berggren et al., "Capacitive Biosensors" *Electroanalysis* 2001, 13(3), 173-180.
Brosel-Oliu et al., Impedimetric Sensors for Bacteria Detection, Chapter 9, Biosensors 2015, pp. 257-288.
Chen et al., "Biomimetic Nanoporous Anodic Alumina Distributed Bragg Reflectors in the Form of Films and Microsized Particles for Sensing Applications" *ACS Applied Materials and Interfaces* 2015, 7, 19816-19824.
Kim et al., "A novel aptamer-based capacitance sensor for real-time and specific detection of *Escherichia coli* and *Salmonella*," Department of Physics, Yonsei University, 2016.
Kim et al., "Wafer-Scale Fabrication of Anodized Aluminum oxide (AAO)—based Nanobiosensor," Department of Physics, Yonsei University, 2016.
Reder-Christ et al., "Biosensor Applications in the Field of Antibiotic Research—A Review of Recent Developments" *Sensors* 2011, 11, 9450-9466.
Sin et al., "Surface Modification of Aluminum Oxide For Biosensing Application" *Biomedical Engineering: Applications, Basis and Communications* 2012, 24(2), 111-116.
Sriram et al., "Current Trends in Nanoporous Anodized Alumina Platforms for Biosensing Applications" *Journal of Nanomaterials* 2016, vol. 2016, 24 pages.

* cited by examiner

*Primary Examiner* — Albert M Navarro
(74) *Attorney, Agent, or Firm* — NORTON ROSE FULBRIGHT US LLP

(57) ABSTRACT

An apparatus for inspecting an antibiotic and a method for determining antibiotic sensitivity using the same is provided. The antibiotic susceptibility inspection time which has conventionally taken longer than 24 hours is shortened to about 2 hours or less, the efficacy of the target substance is monitored in real time, the identification of the microorganism, the kind of the antibiotic capable of treating the microorganism, and the minimum dosage thereof are quickly confirmed. Microbial infections requiring prompt diagnosis and treatment can be effectively treated.

18 Claims, 10 Drawing Sheets

Specification includes a Sequence Listing.

CAPACITIVE BIOSENSOR FOR IDENTIFYING A MICROORGANISM OR DETERMINING ANTIBIOTIC SUSCEPTIBILITY

CROSS-REFERENCE TO RELATED APPLICATION

This application is a divisional of U.S. patent application Ser. No. 15/675,953, filed Aug. 14, 2017, which claims priority to and the benefit of Korean Patent Application No. 10-2016-0103015, filed on Aug. 12, 2016. The disclosures of the aforementioned applications are incorporated herein by reference in their entirety.

SEQUENCE LISTING

The instant application contains a Sequence Listing which has been filed electronically in ASCII format and is hereby incorporated by reference in its entirety. Said ASCII copy, created on Jan. 25, 2021, is named SequenceListing.txt and is 1,528 bytes in size.

BACKGROUND

1. Field of the Disclosure

The present disclosure relates to a capacitive biosensor, and more particularly, relates to a biosensor able to determine antibiotic susceptibility of a microorganism or identify a microorganism according to the result of determining a level of capacitance, changed by microorganisms, in real time.

2. Discussion of Related Art

An inspection to detect antibiotics that can inhibit bacterial growth is known as an antibiotic susceptibility inspection. An antibiotic susceptibility inspection is a direct and important inspection allowing a type of antibiotic to counter a bacterium to be selected. In addition, when prescribing appropriate antibiotics to a patient, such an inspection may enable a customized prescription, considering the prescription method, frequency, cost, and side effects to be made. Using antibiotic susceptibility inspection results, it is possible to reduce increases in treatment costs and the disappointment of patient caregivers in the case that empiric antibiotics are prescribed, providing opportunities for patients to acquire bacterial resistance, reducing complications, and reducing patient recovery periods.

The most common antibiotic susceptibility inspections are the disk diffusion method and the broth dilution method. However, these methods require a process of culturing a bacterium for several days, identifying the bacterium, and measuring turbidity, which may take a long time and requires an excessive amount of labor.

Therefore, there is a need to develop methods to overcome the problems of conventional antimicrobial susceptibility inspection methods by enabling real-time measurement, shortening test times and reducing labor requirements.

SUMMARY OF THE DISCLOSURE

In order to solve the above problems, an object of the present disclosure is to provide a capacitive biosensor capable of measuring antibiotic susceptibility of microorganisms or identifying microorganisms by real-time measurement of capacitance change corresponding to the growth of microorganisms, and methods for measuring antibiotic susceptibility of a microorganism and identifying a microorganism using a biosensor.

In order to achieve the above object, the present disclosure provides a copacitive biosenor for identifying a microorganism or determining an antibiotic susceptibility, the copacitive biosenor for identifying a microorganism or inspecting an antibiotic susceptibility includes, a substrate including anodic aluminum oxide; an electrode layer formed on the substrate and including an interdigitated first electrode and an interdigitated second electrode; and an aptamer fixed to the substrate and specifically bound to the microorganism.

In addition, the present disclosure provides a method for determining an antibiotic susceptibility of the microorganism, the method includes, binding microorganisms to the biosensor; treating the microorganism-bound biosensor with an antibiotic; and determining a change in capacitance after the antibiotic treatment.

In addition, the present disclosure provides a method for identifying a microorganism, the method includes, treating a sample containing a microorganism in the biosensor; confirming whether the microorganism in the sample and aptamer are bound to each other by determining a capacitance change after the sample treatment; and identifying the microorganism.

Using the biosensor and the method for measuring antibiotic susceptibility, an antibiotic susceptibility inspection time which has conventionally taken longer than 24 hours can be shortened to about 2 hours or less, since the time required for identifying microorganisms can be shortened, microorganisms can be identified quickly, a type of antibiotic and a minimum antibiotic concentration necessary for administration can be quickly confirmed, whereby microbial infections requiring prompt diagnosis and treatment can be effectively treated.

DETAILED DESCRIPTION OF EXEMPLARY EMBODIMENTS

Figure 1:
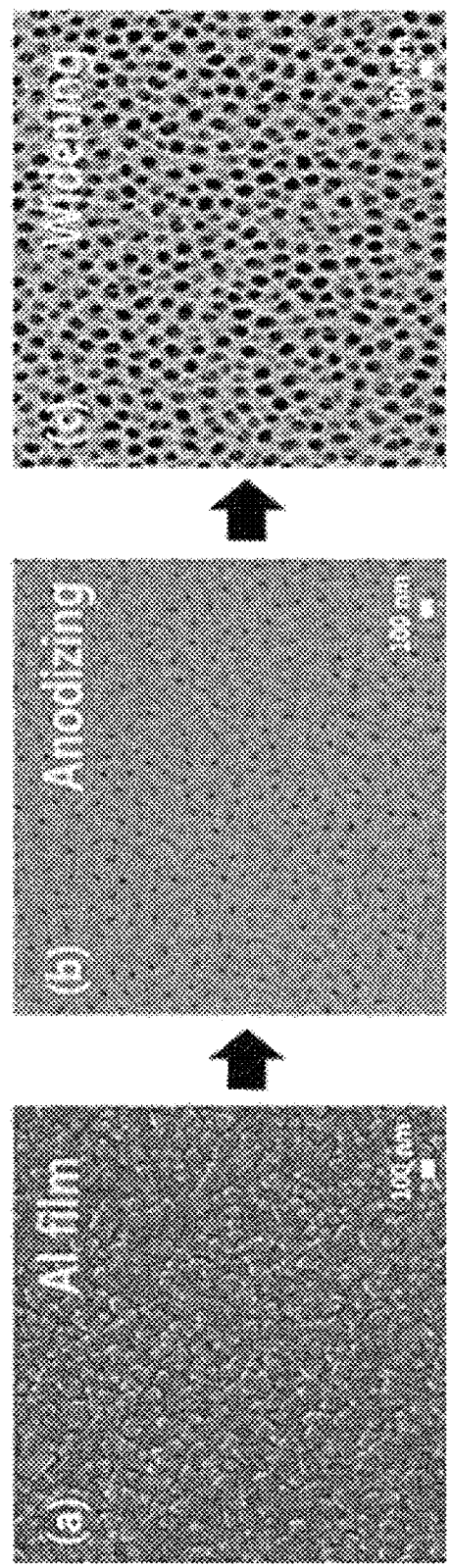
FIG. 1 is an electron microscope image illustrating the process of widening (c) using phosphoric acid immediately after anodic oxidation (b) using an oxalic acid on a film-like aluminum surface (a).
Figure 2:
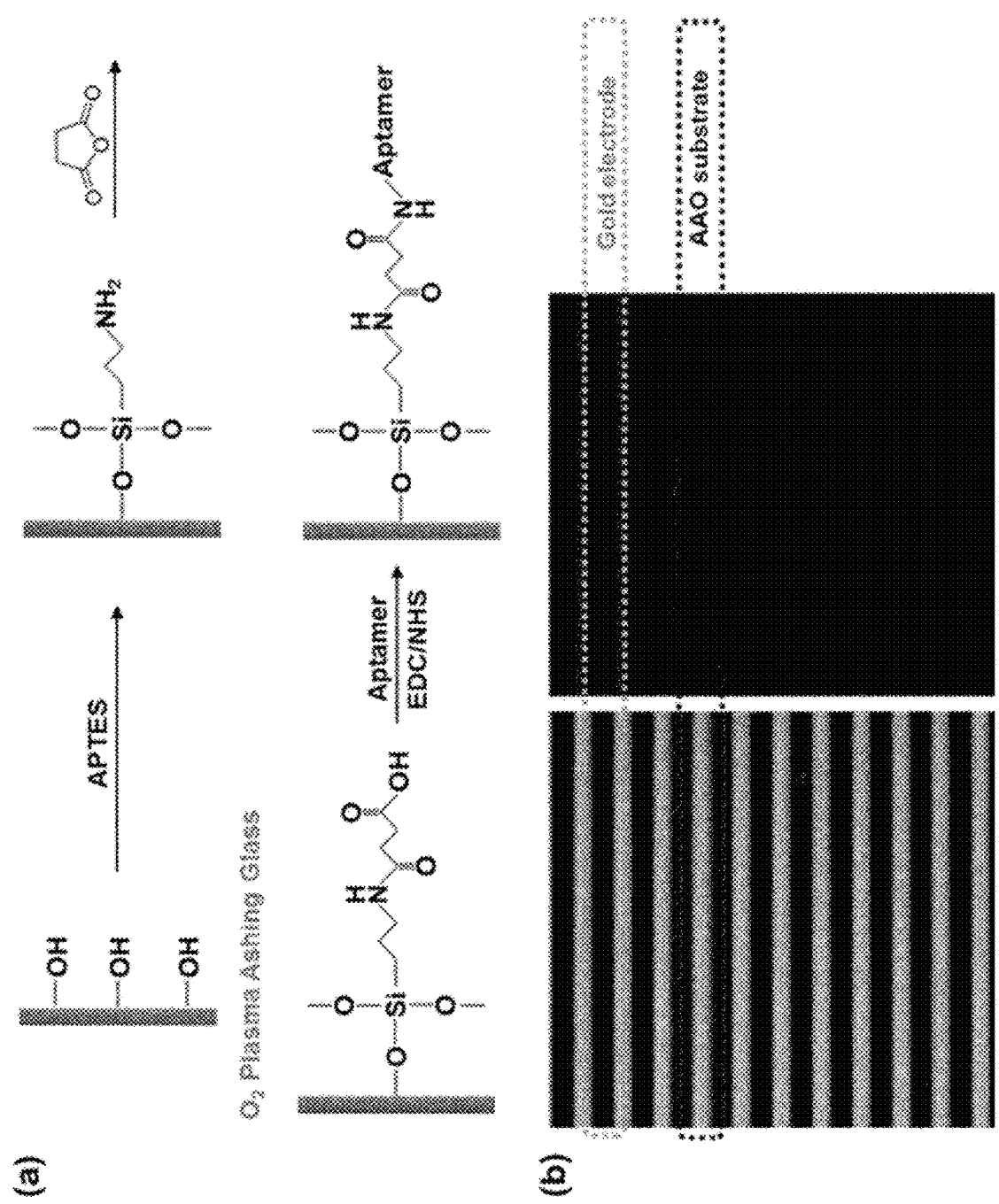
FIG. 2 (a) is a schematic view illustrating a process of introducing a —COOH group to the surface of anodic aluminum oxide and bonding it to an —NH$_2$ group of the aptamer, while (b) is an optical image (left) and a fluorescence image (right) illustrating an anodic aluminum oxide substrate and a gold electrode fixed to an anodic aluminum oxide substrate fixed to a fluorescence-coupled aptamer prepared according to an embodiment of the present disclosure and a gold electrode.

The present disclosure provides a capacitive biosensor and a method for measuring antibiotic susceptibility using the biosensor and a method for identifying a microorganism.

According to the conventional antibiotic susceptibility inspection method, since susceptibility can be confirmed by spreading the bacterium on an entire culture medium, and culturing the bacterium while being treated with antibiotics for about one day, the time required to culture the microorganism to obtain a sufficient amount of microorganism, the time required to confirm reactivity, and a consumption of labor power are relatively large. However, when using the biosensor of the present disclosure, since it is possible to confirm a result in real time by measuring the change in capacitance, the preparation time for measuring/identifying can be shortened, and the sensitivity is high, so that low level changes can be detected in a small amount of sample.

Hereinafter, the present disclosure will be described in detail.

The present disclosure, however, is capable of having numerous iterations and various forms, and the specific embodiments and descriptions set forth below are merely intended to assist in gaining an understanding of the disclosure, while not being intended to limit the disclosure to the specific forms of disclosure. It is to be understood that the scope of the present disclosure includes all changes, equivalents, and alternatives falling within the spirit and scope of the present disclosure.

The capacitive biosensor of the present disclosure is for identifying a microorganism by measuring a change in capacitance in real time caused by coupling of a microorganism to a biosensor, or measuring susceptibility of a microorganism to an antibiotic, measured by a change in capacitance of the microorganism in real time, caused by separation or deformation of a microorganism from an aptamer by an antibiotic. Preferably, the microorganism may be combined with an aptamer of the biosensor of the present disclosure.

The capacitive biosensor of the present disclosure may comprise a substrate including anodic aluminum oxide; an electrode layer formed on the substrate and including an interdigitated first electrode and an interdigitated second electrode; and an aptamer fixed to the substrate and specifically bound to the microorganism.

The biosensor of the present disclosure refers to a device or an apparatus for examining a property of a substance using a function of an organism, the electrode is specifically formed on a substrate, particularly, and refers to a sensor in which an electrode is formed on a substrate, and detects whether binding/separation of substances has occurred by measuring the change in capacitance caused by the binding of the target material between the electrodes using an electrical method, and more particularly, may be a device or an apparatus for measuring capacitance according to the ability of the microorganism to grow in an antibiotic environment, confirming the susceptibility of the microorganism to the antibiotic according to the result. Alternatively, it may be a device or an apparatus capable of identifying a microorganism according to whether an unknown microorganism is bound in a sample using characteristics of an aptamer that specifically binds to the specific microorganism.

In the present disclosure, a substance identified by a biosensor or capable of measuring antibiotic susceptibility includes both microorganisms and biomolecules thereof and the like, particularly, the type of the microorganism is not particularly limited.

Hereinafter, in an embodiment of the present disclosure, it was confirmed that microorganisms can be identified by measurement of capacitance changes and antibiotic susceptibility of bacterium can be detected in real time by using aptamer specific to *E. coli* and *Salmonella*, respectively (FIG. 8 to FIG. 11).

Antibiotic susceptibility is also referred to as antibiotic sensitivity, and the microorganism (for example, a strain, or the like) is affected by the inhibition of growth by the specific antibiotic. According to a method of inspecting typical antibiotic susceptibility, it is said that when an antibiotic is provided and a bacterium does not grow around the location provided with the antibiotic, the bacterium has sensitivity. A result of antibiotic susceptibility inspection can be divided into, for example, susceptibility, intermediate susceptibility (intermediate tolerance) and resistance (tolerance). A susceptible antibiotic is used to treat an infection caused by microorganisms, an infection of a susceptible read-out strain means that the strain can be treated with a recommended amount of an antimicrobial agent for the infection of the species and its site, an infection of the intermediate susceptible (or intermediate tolerance) read-out strain means that the minimum inhibitory concentration of the antimicrobial agent against the inspection strain is similar to that of the blood or tissue, and therefore the treatment effect is lower than that for the susceptible strains, this means that there is a therapeutic effect, when the infected area of the antimicrobial agent, such as the urine, is concentrated, or when the maximum amount of the drug capable of administering a large amount of the antimicrobial agent is administered, and an infection of the resistant (or tolerant) read-out strain means that the blood concentration of the antimicrobial agent when administered at a normal dose has no therapeutic effect.

In the present disclosure, an identification (or identifying) means performing confirmation of species, properties, and the like of a microorganism contained in a sample requiring inspection or analysis, and an identification (or identifying) of a microorganism means identifying the species or the like of the microorganism contained in the sample.

In the present disclosure, a sample is a substance, presumed to contain or contain a target substance, to be analyzed, and may be in the form of a composition, and may be collected from any one of liquid, soil, air, food, waste, plant and animal intestines and animal and plant tissues, blood, urine, tears, saliva, the animal or plant includes a human body.

A biosensor according to an embodiment of the present disclosure can identify a microorganism using an aptamer that specifically binds to a microorganism, and can directly measure an antibiotic sensitivity and a minimum concentration of the identified microorganism. Thus, it is possible to carry out identifying a microorganism and measuring susceptibility thereof, simultaneously. In addition, the biosensor according to an embodiment of the present disclosure has an advantage of being able to provide data on a more precise dosage/concentration of an antibiotic to treat an infection, since minute levels of change can be detected through measuring a change in capacitance.

In the present disclosure, an aptamer refers to a small single-stranded oligonucleotide capable of specifically recognizing a target substance with high affinity or specific affinity.

The biosensor of the present disclosure includes a substrate comprising an anodized aluminum (or ananodic aluminum oxide, AAO), preferably, a substrate made of AAO. The anodic aluminum oxide (AAO) refers to porous alumina in which nano-sized pores having regularity on a surface are formed using anodic oxidation to electrochemically oxidize aluminum. An anodic aluminum oxide may be prepared by: i) anodizing an aluminum surface with an acid treatment; and ii) extending a porous nanostructure. Particularly, the acid is preferably oxalic acid, but is not limited thereto.

When an aptamer is bonded to a nanometer-sized porous nanostructure on the surface of the thin film layer and used as a sensor, it is possible to bind more aptamers than in the case of using other substrates, and it is possible to measure capacitance with higher sensitivity when the same amount of samples are used, therefore, it is confirmed that the performance of the biosensor can be remarkably improved through an embodiment of the present disclosure.

Since types of microorganism which specifically bind are different, depending on a type of the aptamer, a microorganism bound according to the type of the aptamer that specifically binds to the specific microorganism can be identified. For example, when an aptamer specifically bound to *Escherichia coli* (*E. coli*) is immobilized on the substrate and a sample containing a microorganism is treated on the sensor, and when the sample contains *E. coli*, then since the change in capacitance will be sensed by the electrode due to a binding of the aptamer and *E. coli* and a proliferation of bound *E. coli*, it is possible to promptly detect the presence of *E. coli* in the sample, a type of microorganism in the sample can be identified through the target specific binding characteristics of the aptamer.

The fixing may be performed through bonding between a —COOH group introduced on the surface of the anodic aluminum oxide and an —NH$_2$ group of the aptamer, particularly, the —COOH group introduced on the surface of the anodic aluminum oxide is formed by: i) introducing a —OH group by treating the surface of the anodic aluminum oxide with an O$_2$ plasma; ii) introducing a —NH$_2$ group by treating 3-aminopropyltriethoxysilane (APTES) on the surface of the anodic aluminum oxide on which the —OH group is introduced; and iii) introducing a —COOH group by treating the surface of the anodic aluminum oxide on which the —NH$_2$ group is introduced with succinic anhydride.

The biosensor of the present disclosure includes an electrode layer, and may particularly include an interdigitated microelectrode. The interdigitated microelectrodes, a bar arranged in a line form one electrode, and two electrodes (the first electrode and the second electrode) may have opposing structures while being engaged with each other. The two electrodes function as an impedance measuring electrodes of a classical form. In a sensor using an interdigitated microelectrode, a spacing distance between the first electrode and the second electrode may be 0.1 μm to 1000 μm, 1 μm to 500 μm, or 10 μm to 100 μm. By adjusting the spacing distance between the first electrode and the second electrode to the above-mentioned range, it is possible to precisely measure even micro-level biomolecules. In addition, a height of each electrode is in a range of 50 nm to 5,000 nm, and a width of each electrode may be in a range of 1 μm to 500 μm, or 10 μm to 100 μm. Each of the electrodes may be independently selected from a group consisting of gold, platinum, carbon, a conductive polymer, and indium tin oxide (ITO).

The biosensor of the present disclosure may include various types of interdigitated microelectrodes, and may include a plurality of the electrodes. The microelectrode may be formed on the substrate.

The aptamer may be fixed to the space between the first electrode and the second electrode, that is, a spaced apart area. The antimicrobial susceptibility of the microorganism is confirmed by measuring the change in the capacitance of the aptamer fixed between the first electrode and the second electrode when the microorganism to be identified binds to the aptamer, or when the bound microorganism is separated or transformed by the antibiotic. The type of microorganism can also be identified.

The biosensor of the present disclosure may further include a storage portion. The storage portion may contain an electrode layer, an antibiotic, and a microorganism therein. In addition, the storage portion may be formed in a direction perpendicular to the substrate. Particularly, when an identification of a microorganism or antibiotic susceptibility is measured using a biosensor, the microorganism or the antibiotic or the like can be treated inside the storage section. The storage portion may have an open top portion.

The storage portion may be made of one or more materials selected from a group consisting of glass, polypropylene (PP), polyethylene terephthalate (PET) and polycarbonate (PC). As a commercially available example, it may be a plastic well. The capacity of the storage portion may be from 10 ul to 1 ml. The microorganism may be treated together with a culture medium, and as such, the storage unit may also include a culture medium for the microorganism.

The culture medium is also referred to as a medium or a nutrient broth, a liquid or a solid material used for proliferation, preservation, or the like of a microorganism. The specific constitution of the culture medium may be different, depending on a type of microorganism. Any liquid form is preferred, and the culture medium may be blood or may include blood.

The microorganism may be a bacterium, and the bacterium is preferably a gram-positive bacterium, a gram-negative bacterium and an antibiotic-resistant bacterium thereof, but is not limited thereto. Particularly, the gram-positive bacterium may be one or more selected from a group consisting of *Bacillus subtilis, Staphylococcus aureus, Enterococcus faecalis*, and *Staphylococcus epidermidis*, the gram-negative bacterium may be one or more selected from a group consisting of *E. coli*, Psedomonasaeruginosa, Acinetobacterbaumannii, and *Salmonella typhimurium*.

In the present disclosure, the antibiotic is not particularly limited by type, and any antibiotic can be used as long as susceptibility is able to be measured using the biosensor of the present disclosure. Particularly, the antibiotic is selected from a group consisting of Gentamicin, Tetracycline, Ampicillin, Erythromycin, Vancomycin, Linezolid, Methicillin, Oxacillin, Cefotaxime, Rifampicin, Amikacin, Kanamycin, Tobramycin, Neomycin, Ertapenem, Doripenem, Imipenem/Cilastatin, Meropenem, Ceftazidime, Cefepime, Ceftaroline, Ceftobiprole, Aztreonam, Piperacillin, Polymyxin B, Colistin, Ciprofloxacin, Levofloxacin, Moxifloxacin, Gatifloxacin, Tigecycline, as well as combinations and a derivatives thereof.

Figure 5:
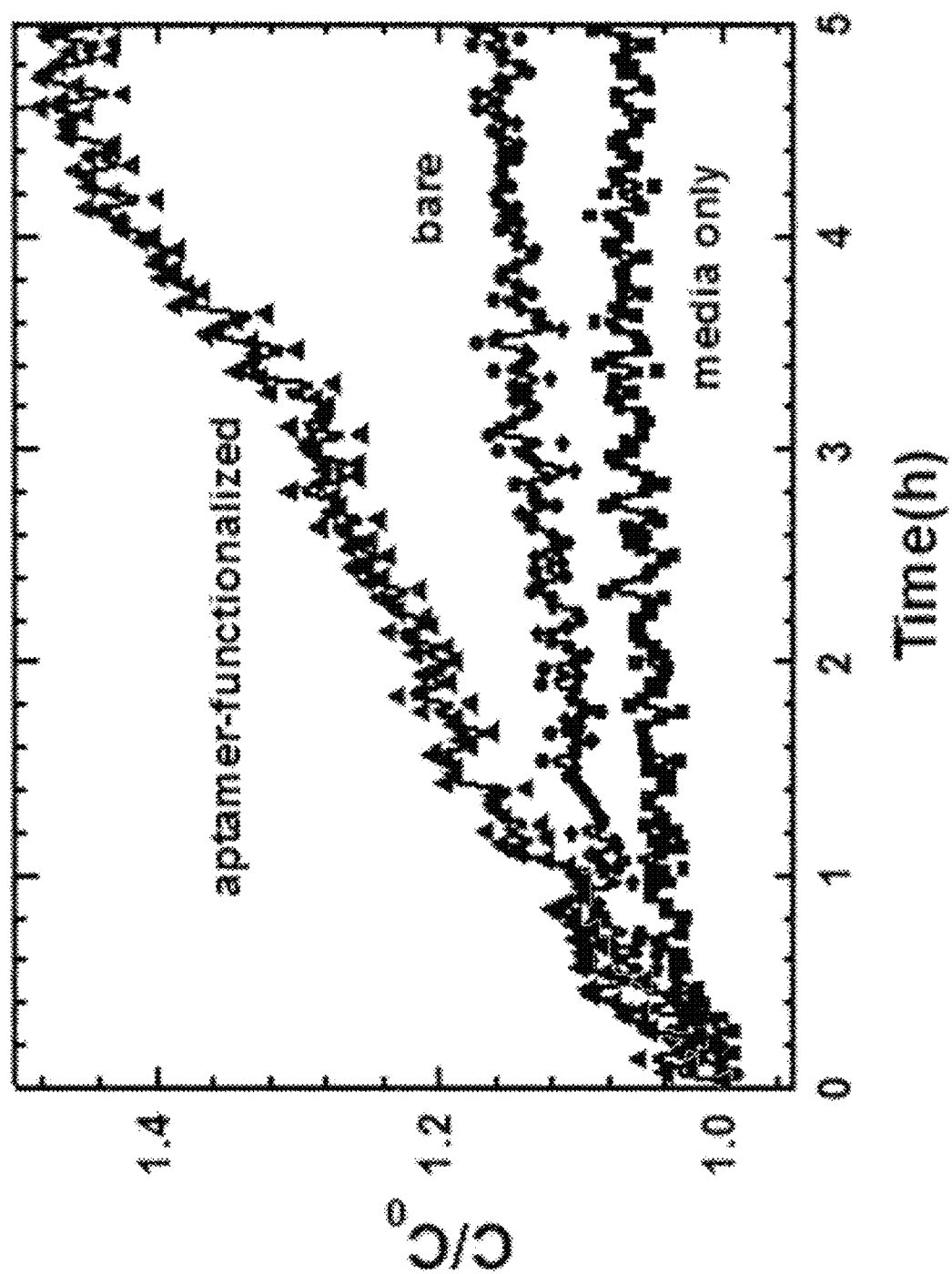
FIG. 5 is a graph illustrating results of performance differences of a biosensor according to a type of a substrate. As a result of measuring a change in capacitance after inserting 105 CFU/ml of an *Escherichia coli* (E. Cole) into the sensor, the blue line represents the biosensor including the AAO substrate+aptamer, the red line represents the biosensor with the aptamer unfixed, and the black line represents the measurement result of the change in capacitance of the culture medium only, without an *E. coli* bacterium.

As shown in FIGS. 1 to 4, when AAO substrate is formed, an electrode is formed thereon and then an aptamer is processed, a surface area capable of specific binding is widened, as compared with the case in which a conventional glass substrate is used, a fixing efficiency of the aptamer is remarkably improved, whereby the sensitivity of the sensor can be increased (FIG. 5 (*a*)).

The biosensor of the present disclosure may further include a wireless transmission unit for transmitting a capacitance measurement result, and a transmission method may be any commonly used method, including both data transmissions using a wired method, such as via USB, or a wireless method, such as a Bluetooth® method.

In addition, the biosensor of the present disclosure can be connected to an LCR meter capable of measuring capacitance to monitor a change in concentration of bacterium in real time. The bacterial sensor may be supplied with a 1 to 100 mV of alternating current voltage having a frequency of 0.1 to 100 KHz.

According to another aspect of the present disclosure, a method for measuring antibiotic susceptibility of a microorganism is provided, comprising: a preparation step of binding microorganisms to the capacitive biosensor; a step of treating the microorganism-bound capacitive biosensor with an antibiotic; and a step of measuring a change in capacitance after an antibiotic treatment.

According to another aspect of the present disclosure, a method for identifying a microorganism is provided, comprising: a step of treating a sample containing a microorganism in the capacitive biosensor; a step of confirming whether the microorganism in the sample and the aptamer are bound to each other by measuring a change in capacitance after the sample treatment; and a step of identifying the microorganism.

The method may further comprise a step of measuring capacitance before the treating the antibiotic in the measuring method or before the treating the sample containing the target microorganism.

The antibiotic sensitivity can be determined by measuring the capacitance value before the antibiotic treatment and the changed capacitance value after the antibiotic treatment and determining whether the microorganisms are killed according to susceptibility in real time, using a change value of the capacitance, and can be measured more precisely through the change in capacitance. For example, the sensitivity to the antibiotic concentration can be measured, so that the minimum amount can be used in the concentration and dose of the antibiotic to be administered for treatment, whereby abuse of antibiotics can be prevented, and side effects can be decreased accordingly.

The biosensor may further include a storage portion for storing an electrode layer, an antibiotic, and a microorganism therein. When the biosensor including the storage portion is used, the antibiotic, the microorganism, and the aptamer may be processed in the storage portion. In this case, high sensitivity can be measured even with a small sample amount.

When the antibiotic of the microorganism is measured by the method for measuring antibiotic susceptibility of the present disclosure, measuring of the selected minimum dose of antibiotics without resistance can be performed quickly, and it is possible to prevent the indiscriminate use of antibiotics and to reduce usage amounts.

Hereinafter, the present disclosure is described in detail with reference to manufacturing examples and experimental examples. The following manufacturing examples and experimental examples are illustrative in the present disclosure and are not intended to limit the scope of the present disclosure.

Manufacturing Example 1: Preparation of Experiment

Cephalothin, chloramphenicol, Gentamicin, Ciprofloxacin, cefrtiaxone, and Tetracycline antibiotics were purchased from Sigma Aldrich (US), and various concentrations were prepared. Chloramphenicol was dissolved in ethanol, Ciprofloxacin was dissolved in DMSO, gentamycin and cephalothin were dissolved in distilled water, and Sephritaxone and Tetracycline were dissolved in ethanol.

The strains used in the experiment were *E. coli*, Acinetobacterbaumannii, *Staphylococcus aureus, Enterococcus faecalis, Enterococcus faecalis*, as well as Ampicillin-resistant *E. coli* and Tetracycline-resistant *E. coli*.

Manufacturing Example 2: Manufacturing of Capacitive Biosensor

In order to manufacture a capacitive biosensor for detecting a microorganism, a sensor (Comparative Example 1) in which electrodes are formed on a glass substrate, a sensor (Comparative Example 2) which a glass electrode formatted and a aptamer-treated sensor, and a sensor (Example 1) treated with an aptamer to AAO were manufactured.

Particularly, the porous nanostructured plate (for example, AAO plate) was formed to have a thickness of Ti/Au/Al (100/20/1000 nm) on a 4-inch Si substrate with a 1 nm thick $SiO_2$ layer grown thereon and a thickness of Ti/Au/Al (100/20/1000 nm).

Then, the porous nanostructured plate was immersed in oxalic acid while maintaining the temperature at 15° C. using a water bath and a chiller at a concentration of 0.3M of oxalic acid, and anodic oxidation was carried out by applying a DC current of 40V. After anodic oxidation, a widening reaction was performed to produce AAO having porous nanostructures. An electron micrograph of the AAO prepared above is shown in FIG. 1.

Figure 3:
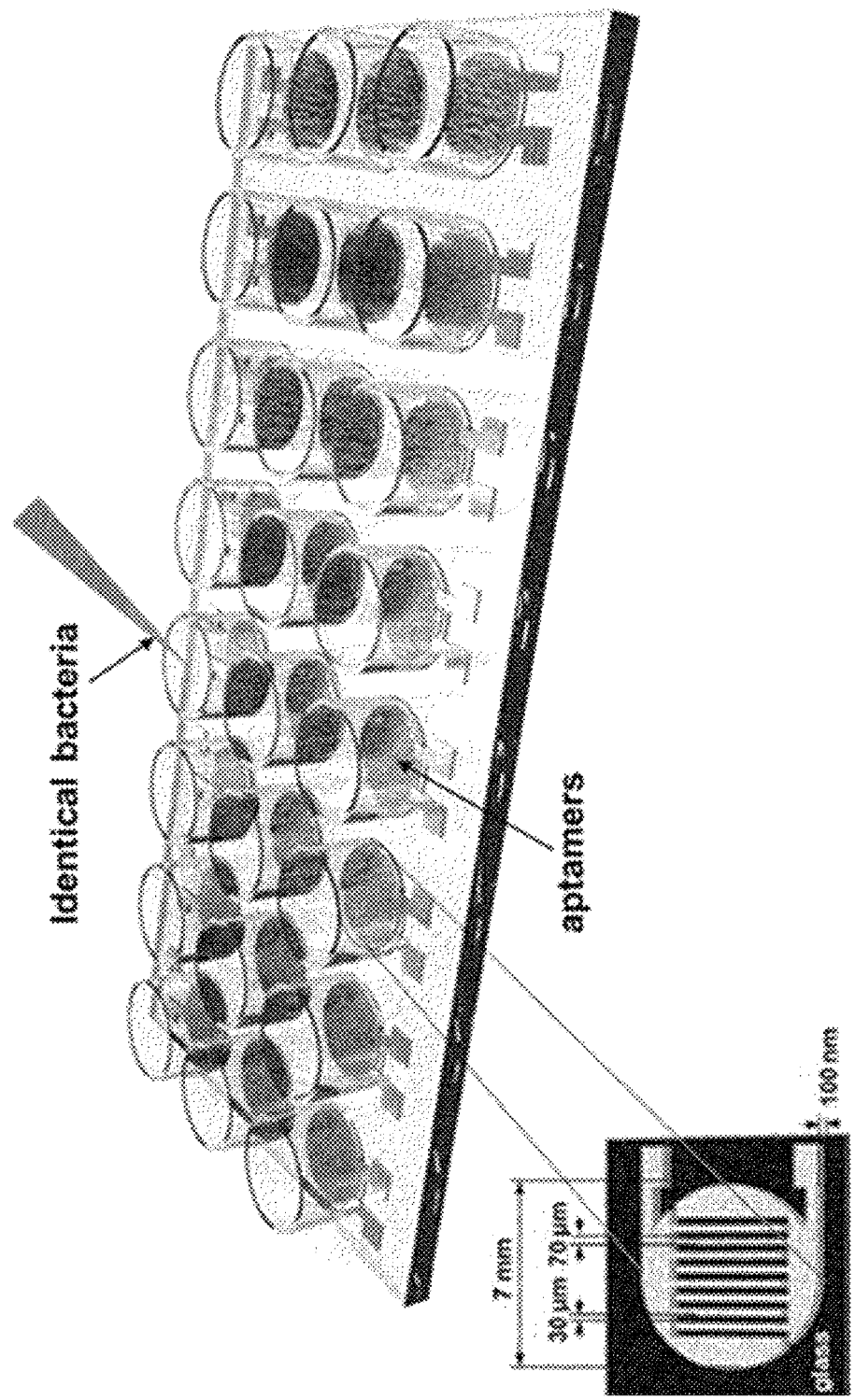
FIG. 3 is a schematic view illustrating a capacitive biosensor array for identifying a microorganism or measuring antibiotic susceptibility of a microorganism manufactured according to an embodiment of the present disclosure.
Figure 4:
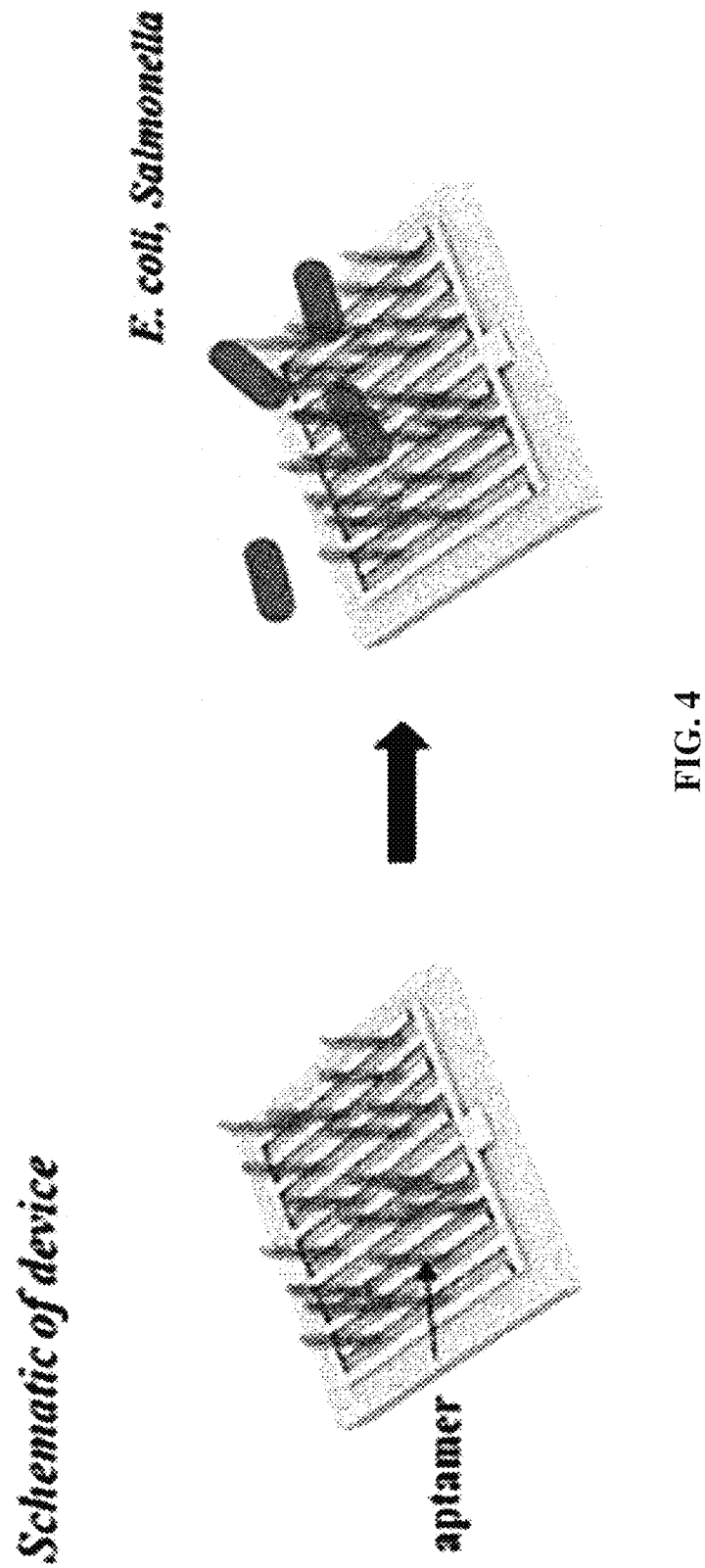
FIG. 4 is a schematic view illustrating a capacitive biosensor array for identifying a microorganism or measuring antibiotic susceptibility of a microorganism manufactured according to an embodiment of the present disclosure, and a process for identifying a microorganism using the same.

The formation of the electrode, as shown in FIG. 3, was produced by depositing Cr with a thickness of 5 nm and Au with a thickness of 40 nm on the AAO plate, manufactured after the anodic oxidation, using a photolithographic process of patterning interdigitated microelectrodes having an electrode width of 70 μm and a spacing distance of 30 μm, with each of bars aligned in a row forming a pole and different electrodes (the first electrode and the second electrode) having a pair structure in which the other poles having opposing polarities face each other. After the produced electrode was sterilized using autoclave and ethanol, a sensor was manufactured by attaching 16 wells to the electrode formed on the substrate for culturing bacterium.

Further, an aptamer for inducing specific binding of *E. coli* was deposited on the substrate. The aptamer may be an *E. coli*-specific aptamer (5'-GCA ATG GTA CGG TAC TTC CCC ATG AGT GTT GTG AAA TGT TGG GAC ACT AGG TGG CAT AGA GCC GCA AAA GTG CAC GCT ACT TTG CTA A-3' (SEQ ID NO: 1), Genotech, Daejeon, Korea), an Asnithobacterbaumannii-specific aptamer (5'-TAC ATG GTC AAC CAA ATT CTT GCA AAT TCT GCA TTC CTA CTG T-3' (SEQ ID NO: 2), Genotech, Daejeon, Korea), a Staphylococcal aptamer-specific aptamer (5'-GCA ATG GTA CGG TAC TTC CTC GGC ACG TTC TCA GTA GCG CTC GCT GGT CAT CCC ACA GCT ACG TCA AAA GTG CAC GCT ACT TTG CTA A-3' (SEQ ID NO: 3), Genotech, Daejeon, Korea), and an *Enterococcus faecalis*-specific aptamer (5'-ATC CAG AGT GAC GCA GCA CGA CAC GTT AGG TTG GTT AGG TTG GTT AGT TTC TTG TGG ACA CGG TGG CTT A-3' (SEQ ID NO: 4), Genotech, Daejeon, Korea) was used.

First, the AAO substrate was treated with $O_2$ plasma to generate an —OH group, and the 3-aminopropyltriethoxysilane (APTES) 10% ethanol solution was treated with the —OH group to replace the —$NH_2$ group. Subsequently, the reaction mixture was treated with a succinic anhydride 0.1 M ethanol solution to convert it to a —COOH group, then the aptamer was immobilized on AAO by reacting with the —$NH_2$ group at the terminal of the aptamer using 1-ethyl-3-(3-dimethylaminopropyl) carbodiimide (EDC) and N-hydroxysuccinimide (NHS).

Experimental Example 1: Confirmation of Measurement Performance of Capacitance Change of Sensor According to Substrate A measurement performance of a capacitance change of a sensor was confirmed using the sensor manufactured according to manufacturing Example 2. Particularly, *E. coli* was treated for each of a sensor (Comparative Example 1) in which an electrode was formed on a glass substrate, a sensor (Comparative Example 2) in which a glass substrate was treated with an aptamer, and a sensor (Example 1) in which AAO was treated with an aptamer, and a change in capacitance was measured.

As shown in FIG. 5, when the capacitance is measured using the sensor of the present disclosure, the change in capacitance is increased as the bacterium binds/propagates, the change in capacitance of all three treatment groups was measured, in the case of the AAO+aptamer sensor of Example 1 as compared to the glass substrate sensor (black) of Comparative Example 1 and the glass substrate sensor (red) treated with the aptamer of Comparative Example 2, it was confirmed that the capacitance increased after 0.5 hours. Particularly, in the case of the AAO+aptamer treatment, the change in capacitance was measured within a short period of time. In the case of the biosensor having the aptamer bonded to the AAO substrate of the present disclosure, the change in capacitance was measured with remarkably high sensitivity.

Experimental Example 2: Identification of a Microorganism

An experiment was conducted to confirm whether a microorganism could be identified using the biosensor produced according to Production Example 2.

Particularly, each well was treated and fixed with an aptamer specific to *E. coli*, Acinetobacterbaumannii, *Staphylococcus aureus* or *Enterococcus faecalis*, and media (a control group or a control) not containing a microorganism, *E. coli*, Acinetobacterbaumannii, *Staphylococcus aureus* or *Enterococcus faecalis* were treated with a sensor, and then the change in capacitance was measured after about 2 hours in an incubator at 37° C.

Figure 6:
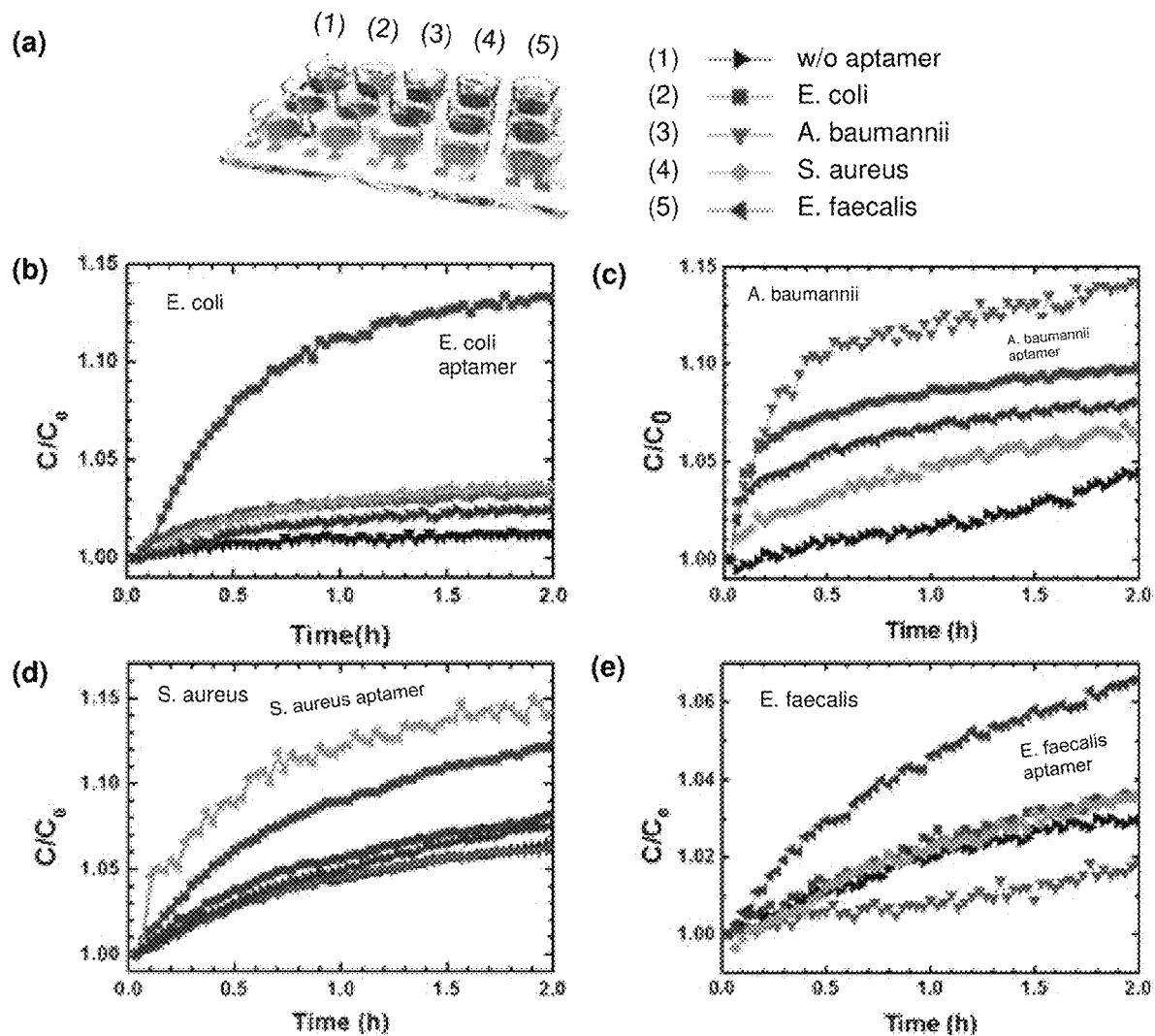
FIG. 6 (a) is a schematic view illustrating a biosensor in which an aptamer is not fixed, or a biosensor in which an aptamer is fixed for each type, and (b) to (e) are a graphs illustrating results of measuring a capacitance change rate in real-time, when *E. coli*, acinetobacterbaumani, *Staphylococcus aureus*, and endorocococcuspecalis are bound to the biosensor in which an aptamer is not fixed or a biosensor in which an aptamer is fixed for each type, respectively.

As shown in FIG. 6 (*b*), when the *E. coli*-specific aptamer was treated, it was confirmed that the change in capacitance was significantly increased during the treatment with *E. coli*. When treating other microorganisms, it was confirmed that the change in capacitance did not occur significantly. On the other hand, as shown in FIG. 6 (*d*), it was confirmed that when a *Staphylococcus aureus*-specific aptamer was treated, a large capacitance change occurred during *Staphylococcus aureus* treatment. When treating other microorganisms, it was confirmed that the change in capacitance did not occur significantly.

Figure 7:
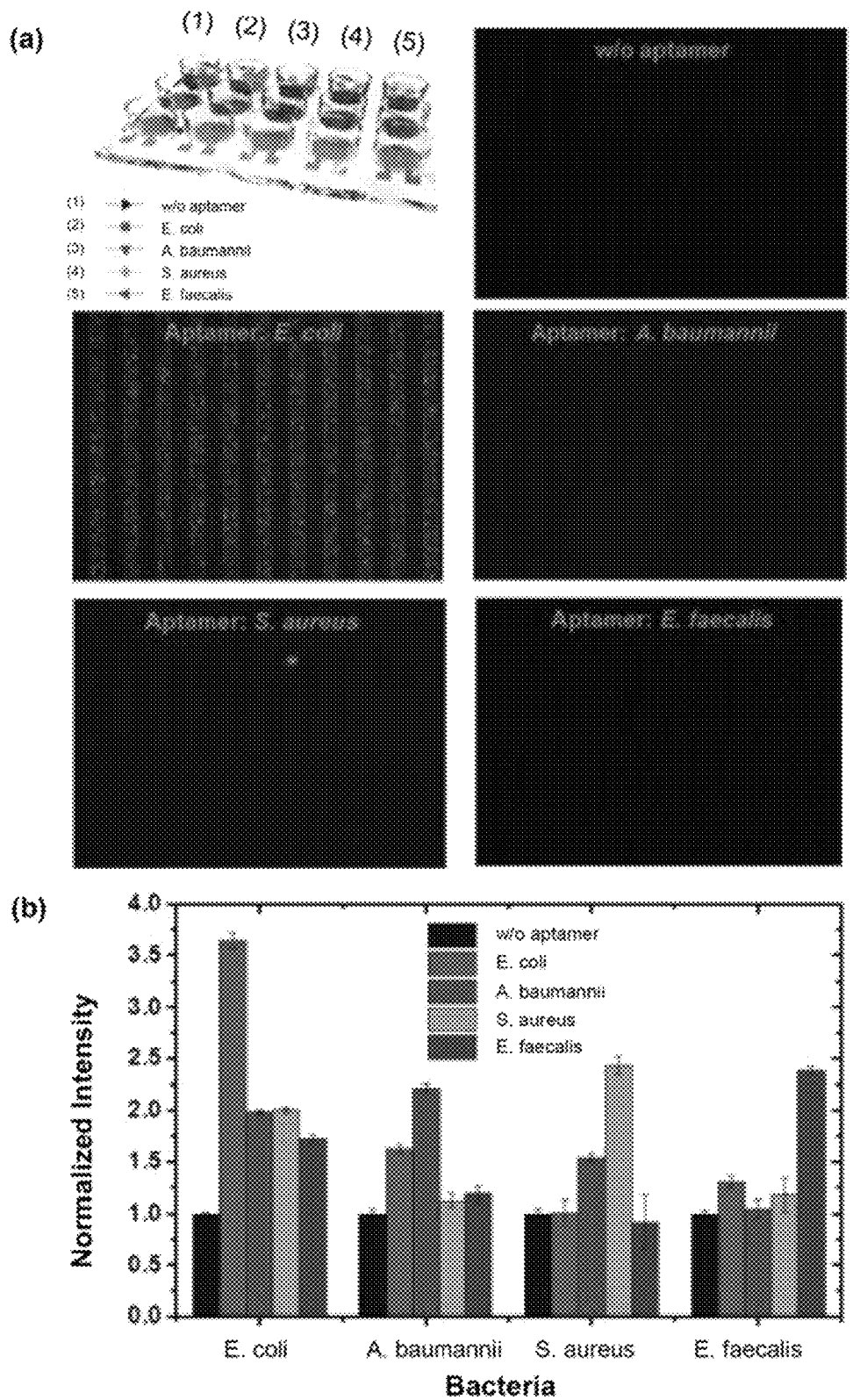
FIG. 7 is a graph illustrating a fluorescent optical image (a) after fluorescence is applied to a bacterium and a graph (b) illustrating the normalized strength thereof, after bonding *E. coli*, acinetobacterbaumani, *Staphylococcus aureus*, and endorocococcuspecalis to the biosensor in which an aptamer is not fixed or the biosensor in which an aptamer is fixed for each type, respectively.

As shown in FIG. 7, when each microorganism is treated with a selective aptamer, when the selective microorganism was treated, it was verified by fluorescence that microorganisms could be identified by confirming that they were attached to the capacitive substrate.

Experimental Example 3: Susceptibility Measurement by Type of Antibiotic

The susceptibility inspection for antibiotics was performed, after identifying an *E. coli* using the capacitive biosensor manufactured by treating *E. coli*-specific aptamer in Experimental Example 2 on the substrate manufactured according to Manufacturing Example 2.

PBS was treated as a control, each treatment was treated with cephalothin, Gentamicin, Ciprofloxacin and chloramphenicol at a concentration of 100 ng/ml, the change in capacitance with time was measured for 6 hours in an incubator at 37° C.

Figure 8:
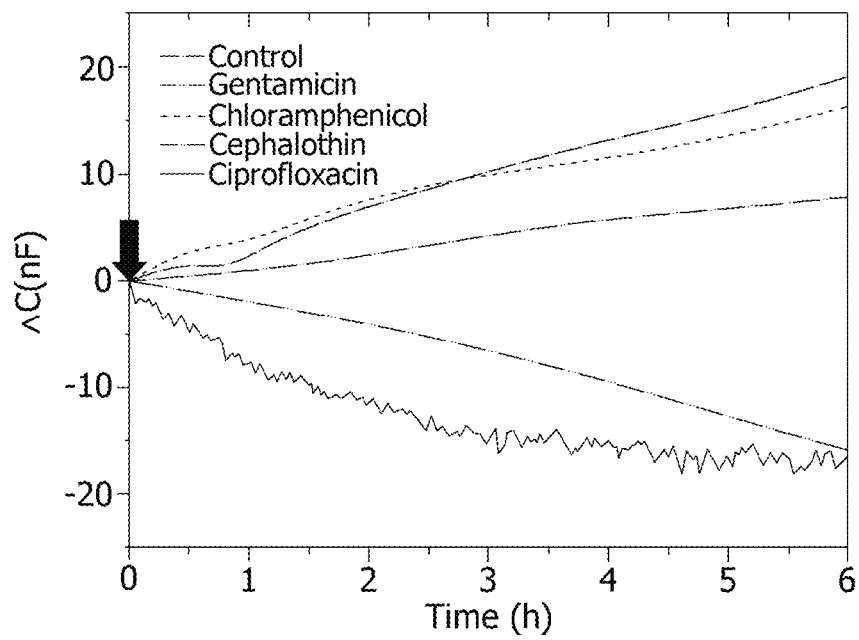
FIG. 8 is a graph illustrating a result of measuring the change in real-time capacitance when various types of antibiotics are treated after *E. coli* is bound to a biosensor to which an aptamer specifically bound to *E. coli* is fixed.

As shown in FIG. 8, when a bacterium was cultured in the sensor and each of the four antibiotics was deposited, there was a difference in the change in capacitance depending on the type of the antibiotic. In the case of chloramphenicol (blue line) and cephalothin (green line), the increase in capacitance after the addition of antibiotics showed the bacterium resistance (tolerance) against the two antibiotics, Ciprofloxacin (pink line) and Gentamicin (red line) showed a decrease in capacitance, and the bacterium was confirmed to have susceptibility to ciprofloxacin and Gentamicin.

Particularly, it can be seen that susceptibility to ciprofloxacin is high, according to the variation width of capacitance.

According to the present disclosure, results can be confirmed within 6 hours, it is possible to quickly measure susceptibility, as the results can be confirmed within 6 hours, it is possible to simultaneously measure several antibiotics, and susceptibility can be measured quickly and simultaneously for several antibiotics.

Experimental Example 4: Inspection of Antibioticminimum Inhibitory Concentration To determine the minimum inhibitory concentration of an antibiotic, E. coli (105 cells/ml) was treated with a capacitive biosensor and grown at 37° C. for 2 hours, and then treated with antibiotic ceftriaxone (MIC: ~ 30 ng/ml) at concentrations of 100, 80, 60, 40 and 20 ng/ml, respectively. The degree of susceptibility was determined based on the results of the capacitance monitored in real time, and the minimum inhibitory concentration thereof was confirmed.

Figure 9:
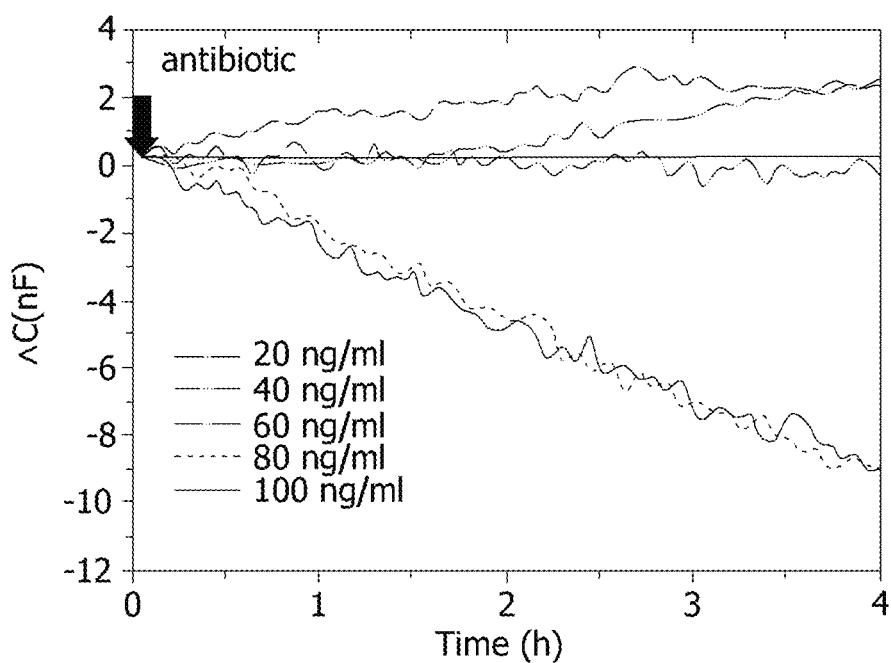
FIG. 9 is a graph illustrating a result of measuring the change in real-time capacitance when various concentrations of ceftriaxone are treated after *E. coli* is bound to a biosensor to which an aptamer specifically bound to *E. coli* is fixed.

As shown in FIG. 9, it can be seen that there is a difference in the change in capacitance of E. coli according to the concentration of antibiotic ceftriaxone, especially, as the change in capacitance value is shown from 40 ng/ml, it can be confirmed that the minimum inhibitory concentration for this E. coli is 40 ng/ml. In addition, since the change is remarkably exhibited within 2 hours after the antibiotic treatment, the minimum antibiotic concentration that can limit tolerance can be quickly confirmed by using the capacitance value of the sensor of the present disclosure.

In addition, E. coli (105 cells/ml) was treated with a capacitive biosensor and grown at 37° C. for 2 hours, and then treated with antibiotic Gentamicin (MIC: ~ 0.5 g/ml) 50, 5, 0.5, 0.05, and 0.005 µg/ml, respectively. The degree of susceptibility was determined based on the results of the capacitance monitored in real time, and the minimum inhibitory concentration thereof was confirmed.

Figure 10:
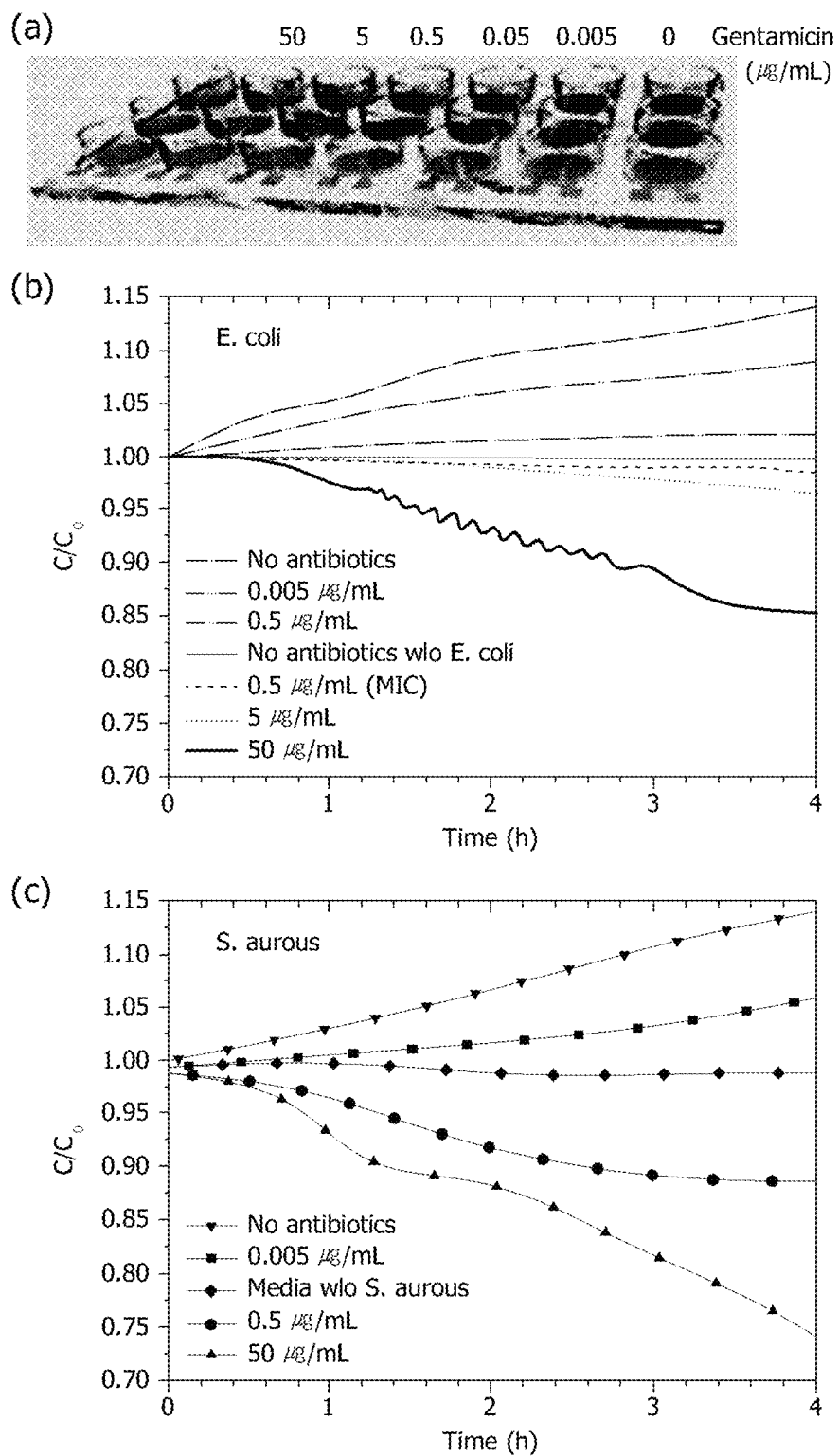
FIG. 10 (a) is a schematic view illustrating a capacitive biosensor for measuring Gentamicin susceptibility of a microorganism, manufactured according to an embodiment of the present disclosure; (b) is a graph illustrating a result of measuring the change in real-time capacitance when various concentrations of Gentamicinare provided or not provided after *E. coli* is bound to a biosensor to which an aptamer specifically bound to *E. coli* is fixed, and; (c) is a graph illustrating a result of measuring the change in real-time capacitance when various concentrations of Gentamicinare provided or not provided after *Staphylococcus* aureusis bound to a biosensor to which an aptamer specifically bound to *Staphylococcus* aureusis fixed.

As shown in FIG. 10 (a) and FIG. 10 (b), it can be seen that there is a difference in the change in capacitance of E. coli according to the concentration of antibiotic Gentamicin, especially, as the change in capacitance value is shown from 0.5 µg/ml, it can be confirmed that the minimum inhibitory concentration for this E. coli is 0.5 µg/ml. In addition, since the change is remarkably exhibited within 2 hours after the antibiotic treatment, the minimum antibiotic concentration that can limit tolerance can be quickly confirmed by using the capacitance value of the sensor of the present disclosure.

In addition, Staphylococcus aureus (105 cells/ml) was treated with a capacitive biosensor and grown at 37° C. for 2 hours, and then was treated with antibiotic Gentamicin (MIC: ~ 0.5 g/ml) 50, 5, 0.5, 0.05, and 0.005 µg/ml, respectively. The degree of susceptibility was determined based on the results of the capacitance monitored in real time, and the minimum inhibitory concentration thereof was confirmed.

As shown in FIG. 10 (a) and FIG. 10 (b), it can be seen that there is a difference in the change in capacitance of E. coli and Staphylococcus aureus according to the concentration of antibiotic Gentamicin, especially, as the change in capacitance value is shown from 0.5 µg/ml, it can be confirmed that the minimum inhibitory concentration for this E. coli is 0.5 µg/ml. In addition, since the change is remarkably exhibited within 2 hours after the antibiotic treatment, the minimum antibiotic concentration that can limit tolerance can be quickly confirmed by using the capacitance value of the sensor of the present disclosure.

In addition, Tetracycline-resistant E. coli or Ampicillin-resistant E. coli (105 cells/ml) was treated with a capacitive biosensor and grown at 37° C. for 2 hours, and was then treated with Tetracycline at a concentration of 2 µg/ml, Gentamicin at a concentration of 1 µg/ml, and Ampicillin at a concentration of 8 µg/ml, respectively. The degree of susceptibility was determined based on the results of the capacitance monitored in real time.

Figure 11:
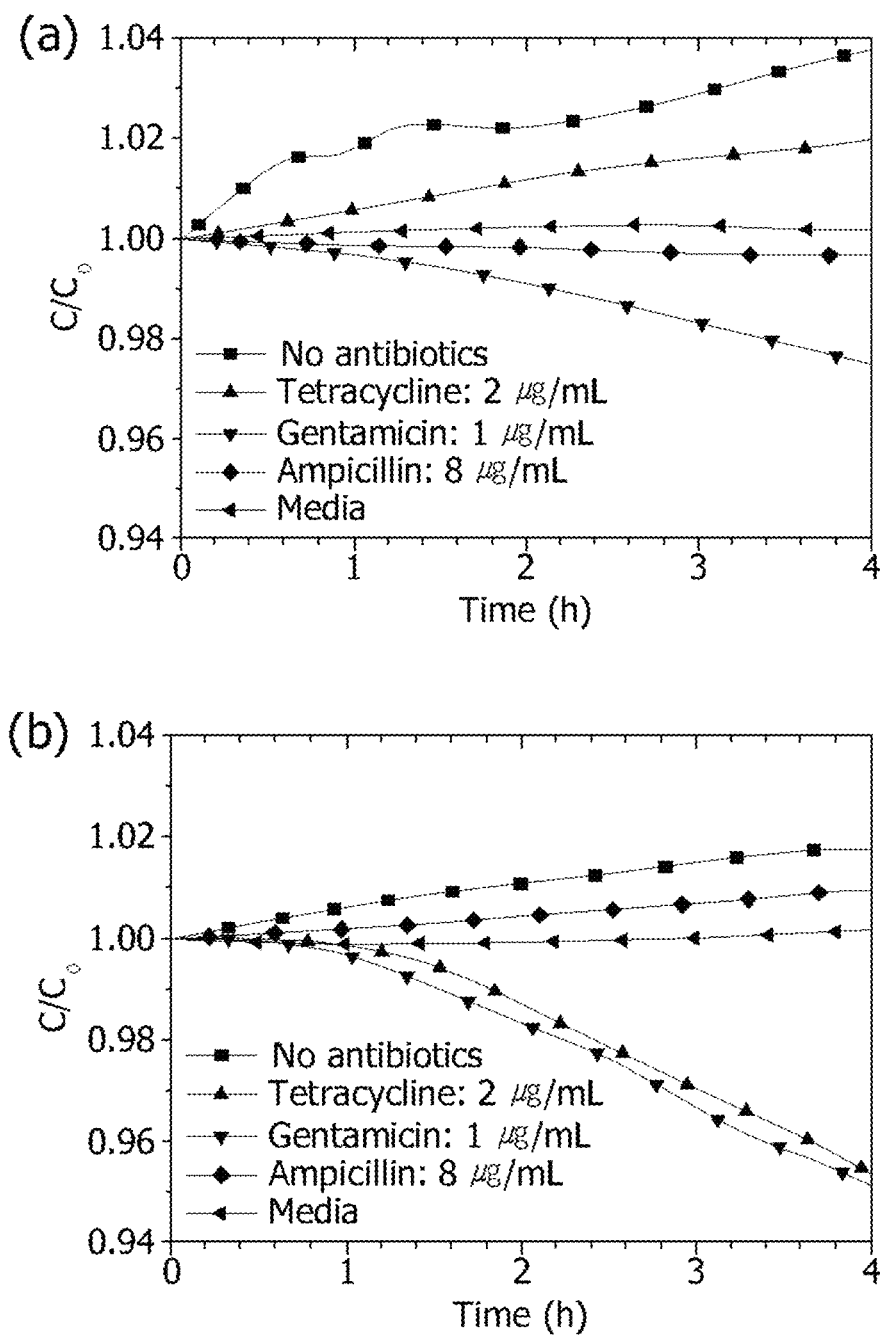
FIG. 11 (a) is a graph illustrating a result of measuring the change in real-time capacitance when an antibiotic (Tetracycline, gentamycin or Ampicillin) is provided or not provided after *E. coli* is bound to a biosensor to which an aptamer specifically bound to Tetracycline-resistant *E. coli* is fixed, and (b) is a graph illustrating a result of measuring the change in real-time capacitance when an antibiotic (Tetracycline, gentamycin or Ampicillin) is provided or not provided after Ampicillin-resistant *E. coli* is bound to a biosensor to which an aptamer specifically bound to Tetracycline-resistant *E. coli* is fixed.

As shown in FIG. 11 (a) and FIG. 11 (b), E. coli, resistant to antibiotics, showed an increase in capacitance value after treatment with each resistant antibiotic, confirming that it did not affect the growth of E. coli. However, for antibiotics not resistant to Gentamicin and the like, the decrease in capacitance value was confirmed to affect the growth of E. coli. The results of this experiment can be used to evaluate resistant antibiotics and antibiotics that can be effectively treated within a short period of time through by measuring AST of antibiotic resistant bacterium.

What is claimed is:

1. A method for determining an antibiotic susceptibility of a microorganism, the method comprising:
   binding the microorganism to a capacitive biosensor, the capacitive biosensor comprising:
   a substrate including an anodic aluminum oxide;
   an electrode layer formed on the substrate and including an interdigitated first electrode and an interdigitated second electrode; and
   an aptamer fixed to the substrate;
   treating the microorganism-bound capacitive biosensor with an antibiotic; and
   determining a change in capacitance after the antibiotic treatment,
   wherein the aptamer is fixed between the first electrode and the second electrode.

2. The method of claim 1, wherein the microorganism is specifically bound by the aptamer of the capacitive biosensor.

3. The method of claim 1, wherein the aptamer is capable of selectively binding the microorganism.

4. The method of claim 1, wherein the microorganism is a bacterium selected from the group consisting of a gram-positive bacterium, a gram-negative bacterium, and an antibiotic resistant bacterium of at least one thereof.

5. The method of claim 1, wherein the antibiotic is selected from the group consisting of a Gentamicin, a Tetracycline, an Ampicillin, an Erythromycin, a Vancomycin, a Linezolid, a Methicillin, an Oxacillin, a Cefotaxime, a Rifampicin, an Amikacin, a Kanamycin, a Tobramycin, a Neomycin, an Ertapenem, a Doripenem, a Imipenem/a Cilastatin, a Meropenem, a Ceftazidime, a Cefepime, a Ceftaroline, a Ceftobiprole, an Aztreonam, a Piperacillin, a Polymyxin B, a Colistin, a Ciprofloxacin, a Levofloxacin, a Moxifloxacin, a Gatifloxacin, a Tigecycline, and combinations and derivatives thereof.

6. The method of claim 1, wherein a change in capacitance after the antibiotic treatment is indicative of antibiotic susceptibility, and wherein determining a change in capacitance after the antibiotic treatment comprises determining a change in capacitance in real time caused by a change in coupling of the microorganism to the capacitive biosensor or a change in capacitance in real time caused by the antibiotic causing a separation or deformation of a microorganism bound to the aptamer.

7. The method of claim 1, further comprising identifying the microorganism.

8. The method of claim 7, wherein the microorganism is identified by a change in capacitance in real time caused by coupling of the microorganism to the capacitive biosensor.

9. The method of claim 1, further comprising determining a minimum growth inhibitory concentration of the antibiotic against the microorganism using the determined change in capacitance after the antibiotic treatment.

10. The method of claim 9, wherein the minimum growth inhibitory concentration for the antibiotic is determined about two hours to about six hours after treating the microorganism-bound capacitive biosensor with the antibiotic.

11. The method of claim 1, wherein the aptamer of the capacitive biosensor is fixed to the substrate of the capacitive biosensor via an amide bond, and wherein the C=O of the amide bond is from the modified anodic aluminum oxide of the substrate and the nitrogen of the amide bond is from the aptamer.

12. The method of claim 1, wherein the anodic aluminum oxide of the capacitive biosensor is formed by:

i) anodizing an aluminum surface with acid treatment; and
ii) extending a porous nanostructure.

13. The method of claim 1, wherein the modified anodic aluminum oxide of the capacitive biosensor comprises a porous nanostructure.

14. The method of claim 1, wherein the C=O group from the modified anodic aluminum oxide of the capacitive biosensor is formed by:
   i) introducing a —OH group by treating a surface of an anodic aluminum oxide with an $O_2$ plasma to form a —OH group on the surface of the anodic aluminum oxide;
   ii) introducing a —$NH_2$ group by treating the —OH group on the surface of the anodic aluminum oxide with 3-aminopropyltriethoxysilane (APTES) to form a —$NH_2$ group on the surface of the anodic aluminum oxide; and
   iii) introducing a —COOH group by treating the —$NH_2$ group on the surface of the anodic aluminum oxide with succinic anhydride to form a COOH group on the surface of the anodic aluminum oxide.

15. The method of claim 1, wherein the modified anodic aluminum oxide of the capacitive biosensor bound to the aptamer of the capacitive biosensor comprises the following structure:

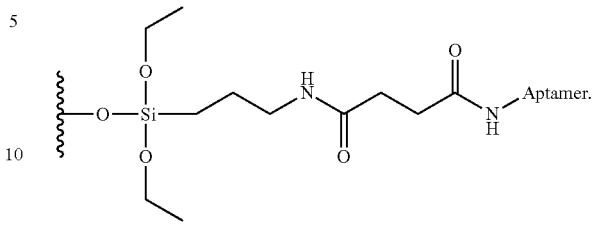

16. The method of claim 1, wherein the aptamer of the capacitive biosensor comprises an oligonucleotide.

17. The method of claim 1, wherein a distance between the first electrode and the second electrode of the capacitive biosensor is 1 μm to 100 μm.

18. The method of claim 1, wherein the capacitive biosensor further comprises a storage portion capable of receiving at least one of an electrode layer, an antibiotic, and a microorganism therein.

* * * * *

SEQUENCE LISTING

<160> NUMBER OF SEQ ID NOS: 4

<210> SEQ ID NO 1
<211> LENGTH: 88
<212> TYPE: DNA
<213> ORGANISM: Artificial Sequence
<220> FEATURE:
<223> OTHER INFORMATION: E. coli-specific aptamer

<400> SEQUENCE: 1
gcaatggtac ggtacttccc catgagtgtt gtgaaatgtt gggacactag gtggcataga      60
gccgcaaaag tgcacgctac tttgctaa      88

<210> SEQ ID NO 2
<211> LENGTH: 43

-continued

```
<212> TYPE: DNA
<213> ORGANISM: Artificial Sequence
<220> FEATURE:
<223> OTHER INFORMATION: Asnithobacterbaumannii-specific aptamer

<400> SEQUENCE: 2
tacatggtca accaaattct tgcaaattct gcattcctac tgt                    43

<210> SEQ ID NO 3
<211> LENGTH: 88
<212> TYPE: DNA
<213> ORGANISM: Artificial Sequence
<220> FEATURE:
<223> OTHER INFORMATION: Staphylococcal aptamer-specific aptamer

<400> SEQUENCE: 3
gcaatggtac ggtacttcct cggcacgttc tcagtagcgc tcgctggtca tcccacagct   60
acgtcaaaag tgcacgctac tttgctaa                                     88

<210> SEQ ID NO 4
<211> LENGTH: 70
<212> TYPE: DNA
<213> ORGANISM: Artificial Sequence
<220> FEATURE:
<223> OTHER INFORMATION: Enterococcus faecalis-specific aptamer

<400> SEQUENCE: 4
atccagagtg acgcagcacg acacgttagg ttggttaggt tggttagttt cttgtggaca   60
cggtggctta                                                         70
```